United States Patent
Specht et al.

(10) Patent No.: US 8,602,993 B2
(45) Date of Patent: Dec. 10, 2013

(54) IMAGING WITH MULTIPLE APERTURE MEDICAL ULTRASOUND AND SYNCHRONIZATION OF ADD-ON SYSTEMS

(75) Inventors: Donald F. Specht, Los Altos, CA (US); Kenneth D. Brewer, Santa Clara, CA (US)

(73) Assignee: Maui Imaging, Inc., Sunnyvale, CA (US)

( * ) Notice: Subject to any disclaimer, the term of this patent is extended or adjusted under 35 U.S.C. 154(b) by 0 days.

(21) Appl. No.: 13/002,778

(22) PCT Filed: Aug. 7, 2009

(86) PCT No.: PCT/US2009/053096
§ 371 (c)(1), (2), (4) Date: Apr. 6, 2011

(87) PCT Pub. No.: WO2010/017445
PCT Pub. Date: Feb. 11, 2010

(65) Prior Publication Data
US 2011/0178400 A1    Jul. 21, 2011

Related U.S. Application Data

(60) Provisional application No. 61/087,571, filed on Aug. 8, 2008, provisional application No. 61/169,264, filed on Apr. 14, 2009.

(51) Int. Cl.
*A61B 8/00* (2006.01)
(52) U.S. Cl.
USPC ........................................... 600/437; 600/443
(58) Field of Classification Search
USPC ................................................ 600/437–445
See application file for complete search history.

(56) References Cited

U.S. PATENT DOCUMENTS

| | | | |
|---|---|---|---|
| 4,097,835 | A | 6/1978 | Green |
| 4,271,842 | A | 6/1981 | Specht et al. |
| 4,333,474 | A | 6/1982 | Nigam |
| 4,339,952 | A | 7/1982 | Foster |

(Continued)

FOREIGN PATENT DOCUMENTS

| | | |
|---|---|---|
| EP | 2058796 A2 | 5/2009 |
| EP | 2101191 A2 | 9/2009 |

(Continued)

OTHER PUBLICATIONS

Specht, Donalf F.; U.S. Appl. No. 13/215,966 entitled "Method and apparatus to produce ultrasonic images using multiple apertures," filed Aug. 23, 2011.

(Continued)

*Primary Examiner* — Long V. Le
*Assistant Examiner* — Farshad Negarestan
(74) *Attorney, Agent, or Firm* — Shay Glenn LLP

(57) ABSTRACT

The benefits of a multi-aperture ultrasound probe can be achieved with add-on devices. Synchronization and correlation of echoes from multiple transducer elements located in different arrays is essential to the successful processing of multiple aperture imaging. The algorithms disclosed here teach methods to successfully process these signals when the transmission source is coming from another ultrasound system and synchronize the add-on system to the other ultrasound system. Two-dimensional images with different noise components can be constructed from the echoes received by individual transducer elements. The disclosed techniques have broad application in medical imaging and are ideally suited to multi-aperture cardiac imaging using two or more intercostal spaces.

26 Claims, 6 Drawing Sheets

(56) References Cited

U.S. PATENT DOCUMENTS

| | | |
|---|---|---|
| 4,501,279 A | 2/1985 | Seo |
| 4,682,497 A | 7/1987 | Sasaki |
| 4,831,601 A | 5/1989 | Breimesser et al. |
| 4,893,628 A | 1/1990 | Angelsen |
| 5,050,588 A | 9/1991 | Grey et al. |
| 5,305,756 A | 4/1994 | Entrekin et al. |
| 5,339,282 A | 8/1994 | Kuhn et al. |
| 5,355,888 A | 10/1994 | Kendall |
| 5,409,010 A | 4/1995 | Beach et al. |
| 5,442,462 A | 8/1995 | Guissin |
| 5,503,152 A | 4/1996 | Oakley et al. |
| 5,515,853 A | 5/1996 | Smith et al. |
| 5,522,393 A | 6/1996 | Phillips et al. |
| 5,558,092 A | 9/1996 | Unger et al. |
| 5,675,550 A | 10/1997 | Ekhaus |
| 5,769,079 A | 6/1998 | Hossack |
| 5,797,845 A | 8/1998 | Barabash et al. |
| 5,798,459 A | 8/1998 | Ohba et al. |
| 5,876,342 A | 3/1999 | Chen et al. |
| 5,916,169 A | 6/1999 | Hanafy et al. |
| 5,964,707 A | 10/1999 | Fenster et al. |
| 6,014,473 A | 1/2000 | Hossack et al. |
| 6,048,315 A | 4/2000 | Chiao et al. |
| 6,056,693 A | 5/2000 | Haider |
| 6,122,538 A | 9/2000 | Sliwa, Jr. et al. |
| 6,129,672 A | 10/2000 | Seward et al. |
| 6,148,095 A | 11/2000 | Prause et al. |
| 6,162,175 A | 12/2000 | Marian, Jr. et al. |
| 6,166,853 A | 12/2000 | Sapia et al. |
| 6,193,665 B1 | 2/2001 | Hall et al. |
| 6,196,739 B1 | 3/2001 | Silverbrook |
| 6,246,901 B1 | 6/2001 | Benaron |
| 6,304,684 B1 | 10/2001 | Niczyporuk et al. |
| 6,324,453 B1 | 11/2001 | Breed et al. |
| 6,361,500 B1 | 3/2002 | Masters |
| 6,394,955 B1 | 5/2002 | Perlitz |
| 6,423,002 B1 | 7/2002 | Hossack |
| 6,449,821 B1 | 9/2002 | Sudol et al. |
| 6,450,965 B2 | 9/2002 | Williams et al. |
| 6,468,216 B1 | 10/2002 | Powers et al. |
| 6,471,650 B2 | 10/2002 | Powers et al. |
| 6,517,484 B1 | 2/2003 | Wilk et al. |
| 6,614,560 B1 | 9/2003 | Silverbrook |
| 6,652,461 B1 | 11/2003 | Levkovitz |
| 6,690,816 B2 | 2/2004 | Aylward et al. |
| 6,695,778 B2 | 2/2004 | Golland et al. |
| 6,702,745 B1 | 3/2004 | Smythe |
| 6,728,567 B2 | 4/2004 | Rather et al. |
| 6,752,762 B1 | 6/2004 | DeJong et al. |
| 6,755,787 B2 | 6/2004 | Hossack et al. |
| 6,780,152 B2 | 8/2004 | Ustuner et al. |
| 6,790,182 B2 | 9/2004 | Eck et al. |
| 6,843,770 B2 | 1/2005 | Sumanaweera |
| 6,854,332 B2 | 2/2005 | Alleyne |
| 6,932,767 B2 | 8/2005 | Landry et al. |
| 7,033,320 B2 | 4/2006 | Von Behren et al. |
| 7,087,023 B2 | 8/2006 | Daft et al. |
| 7,217,243 B2 | 5/2007 | Takeuchi |
| 7,221,867 B2 | 5/2007 | Silverbrook |
| 7,231,072 B2 | 6/2007 | Yamano et al. |
| 7,269,299 B2 | 9/2007 | Schroeder |
| 7,313,053 B2 | 12/2007 | Wodnicki |
| 7,366,704 B2 | 4/2008 | Reading et al. |
| 7,402,136 B2 | 7/2008 | Hossack et al. |
| 7,410,469 B1 | 8/2008 | Talish et al. |
| 7,415,880 B2 | 8/2008 | Renzel |
| 7,443,765 B2 | 10/2008 | Thomenius et al. |
| 7,447,535 B2 | 11/2008 | Lavi |
| 7,466,848 B2 | 12/2008 | Metaxas et al. |
| 7,469,096 B2 | 12/2008 | Silverbrook |
| 7,474,778 B2 | 1/2009 | Shinomura et al. |
| 7,481,577 B2 | 1/2009 | Ramamurthy et al. |
| 7,491,171 B2 | 2/2009 | Barthe et al. |
| 7,497,828 B1 | 3/2009 | Wilk et al. |
| 7,497,830 B2 | 3/2009 | Li |
| 7,510,529 B2 | 3/2009 | Chou et al. |
| 7,514,851 B2 | 4/2009 | Wilser et al. |
| 7,549,962 B2 | 6/2009 | Dreschel et al. |
| 7,574,026 B2 | 8/2009 | Rasche et al. |
| 7,625,343 B2 | 12/2009 | Cao et al. |
| 7,637,869 B2 | 12/2009 | Sudol |
| 7,668,583 B2 | 2/2010 | Fegert et al. |
| 7,674,228 B2 | 3/2010 | Williams et al. |
| 7,699,776 B2 | 4/2010 | Walker et al. |
| 7,722,541 B2 | 5/2010 | Cai |
| 7,744,532 B2 | 6/2010 | Ustuner et al. |
| 7,785,260 B2 | 8/2010 | Umemura et al. |
| 7,787,680 B2 | 8/2010 | Ahn et al. |
| 7,806,828 B2 | 10/2010 | Stringer |
| 7,819,810 B2 | 10/2010 | Stringer et al. |
| 7,824,337 B2 | 11/2010 | Abe et al. |
| 7,833,163 B2 | 11/2010 | Cai |
| 7,837,624 B1 | 11/2010 | Hossack et al. |
| 7,846,097 B2 | 12/2010 | Jones et al. |
| 7,850,613 B2 | 12/2010 | Stribling |
| 7,862,508 B2 | 1/2011 | Davies et al. |
| 7,876,945 B2 | 1/2011 | Lötjönen |
| 7,887,486 B2 | 2/2011 | Ustuner et al. |
| 7,901,358 B2 | 3/2011 | Mehi et al. |
| 7,919,906 B2 | 4/2011 | Cerofolini |
| 7,926,350 B2 | 4/2011 | Kröning et al. |
| 7,927,280 B2 | 4/2011 | Davidsen |
| 7,972,271 B2 | 7/2011 | Johnson et al. |
| 7,984,651 B2 | 7/2011 | Randall et al. |
| 8,002,705 B1 | 8/2011 | Napolitano et al. |
| 8,057,392 B2 | 11/2011 | Hossack et al. |
| 8,057,393 B2 | 11/2011 | Yao et al. |
| 8,079,263 B2 | 12/2011 | Randall et al. |
| 8,079,956 B2 | 12/2011 | Azuma et al. |
| 8,088,067 B2 | 1/2012 | Vortman et al. |
| 8,088,068 B2 | 1/2012 | Yao et al. |
| 8,088,071 B2 | 1/2012 | Hwang et al. |
| 8,135,190 B2 | 3/2012 | Bae et al. |
| 8,157,737 B2 | 4/2012 | Zhang et al. |
| 8,182,427 B2 | 5/2012 | Wu et al. |
| 8,202,219 B2 | 6/2012 | Luo et al. |
| 2002/0035864 A1 | 3/2002 | Paltieli et al. |
| 2002/0087071 A1 | 7/2002 | Schmitz et al. |
| 2002/0111568 A1 | 8/2002 | Bukshpan |
| 2003/0028111 A1 | 2/2003 | Vaezy et al. |
| 2003/0040669 A1 | 2/2003 | Grass et al. |
| 2003/0228053 A1 | 12/2003 | Li et al. |
| 2004/0068184 A1 | 4/2004 | Trahey et al. |
| 2004/0100163 A1 | 5/2004 | Baumgartner et al. |
| 2004/0111028 A1 | 6/2004 | Abe et al. |
| 2004/0122313 A1 | 6/2004 | Moore et al. |
| 2004/0122322 A1 | 6/2004 | Moore et al. |
| 2004/0127793 A1 | 7/2004 | Mendlein et al. |
| 2004/0138565 A1 | 7/2004 | Trucco |
| 2004/0144176 A1 | 7/2004 | Yoden |
| 2004/0236223 A1 | 11/2004 | Barnes et al. |
| 2005/0004449 A1 | 1/2005 | Mitschke et al. |
| 2005/0053305 A1 | 3/2005 | Li et al. |
| 2005/0054910 A1 | 3/2005 | Tremblay et al. |
| 2005/0090743 A1 | 4/2005 | Kawashima et al. |
| 2005/0113694 A1 | 5/2005 | Haugen et al. |
| 2005/0147297 A1 | 7/2005 | McLaughlin et al. |
| 2005/0240125 A1 | 10/2005 | Makin et al. |
| 2005/0281447 A1 | 12/2005 | Moreau-Gobard et al. |
| 2005/0288588 A1 | 12/2005 | Weber et al. |
| 2006/0062447 A1 | 3/2006 | Rinck et al. |
| 2006/0074313 A1 | 4/2006 | Slayton et al. |
| 2006/0074315 A1 | 4/2006 | Liang et al. |
| 2006/0079759 A1 | 4/2006 | Vaillant et al. |
| 2006/0079778 A1 | 4/2006 | Mo et al. |
| 2006/0079782 A1 | 4/2006 | Beach et al. |
| 2006/0094962 A1 | 5/2006 | Clark |
| 2006/0122506 A1 | 6/2006 | Davies et al. |
| 2006/0173327 A1 | 8/2006 | Kim |
| 2007/0016022 A1 | 1/2007 | Blalock et al. |
| 2007/0016044 A1 | 1/2007 | Blalock et al. |
| 2007/0036414 A1 | 2/2007 | Georgescu et al. |
| 2007/0055155 A1 | 3/2007 | Owen et al. |
| 2007/0078345 A1 | 4/2007 | Mo et al. |

(56) References Cited

U.S. PATENT DOCUMENTS

| | | |
|---|---|---|
| 2007/0088213 A1 | 4/2007 | Poland |
| 2007/0161904 A1 | 7/2007 | Urbano |
| 2007/0167752 A1 | 7/2007 | Proulx et al. |
| 2007/0232914 A1 | 10/2007 | Chen et al. |
| 2007/0238999 A1 | 10/2007 | Specht |
| 2007/0242567 A1 | 10/2007 | Daft et al. |
| 2008/0103393 A1 | 5/2008 | Specht |
| 2008/0110261 A1 | 5/2008 | Randall et al. |
| 2008/0110263 A1 | 5/2008 | Klessel et al. |
| 2008/0112265 A1 | 5/2008 | Urbano et al. |
| 2008/0114241 A1 | 5/2008 | Randall et al. |
| 2008/0114245 A1 | 5/2008 | Randall et al. |
| 2008/0114246 A1 | 5/2008 | Randall et al. |
| 2008/0114247 A1 | 5/2008 | Urbano et al. |
| 2008/0114248 A1 | 5/2008 | Urbano et al. |
| 2008/0114249 A1 | 5/2008 | Randall et al. |
| 2008/0114250 A1 | 5/2008 | Urbano et al. |
| 2008/0114251 A1 | 5/2008 | Weymer et al. |
| 2008/0114252 A1 | 5/2008 | Randall et al. |
| 2008/0114253 A1 | 5/2008 | Randall et al. |
| 2008/0114255 A1 | 5/2008 | Schwartz et al. |
| 2008/0125659 A1 | 5/2008 | Wilser et al. |
| 2008/0181479 A1 | 7/2008 | Yang et al. |
| 2008/0188747 A1 | 8/2008 | Randall et al. |
| 2008/0188750 A1 | 8/2008 | Randall et al. |
| 2008/0194957 A1 | 8/2008 | Hoctor et al. |
| 2008/0194958 A1 | 8/2008 | Lee et al. |
| 2008/0194959 A1 | 8/2008 | Wang et al. |
| 2008/0208061 A1 | 8/2008 | Halmann |
| 2008/0242996 A1 | 10/2008 | Hall et al. |
| 2008/0249408 A1 | 10/2008 | Palmeri et al. |
| 2008/0255452 A1 | 10/2008 | Entrekin |
| 2008/0269613 A1 | 10/2008 | Summers et al. |
| 2008/0275344 A1 | 11/2008 | Glide-Hurst et al. |
| 2008/0285819 A1 | 11/2008 | Konofagou et al. |
| 2008/0294045 A1 | 11/2008 | Ellington et al. |
| 2008/0294050 A1 | 11/2008 | Shinomura et al. |
| 2008/0294052 A1 | 11/2008 | Wilser et al. |
| 2008/0306382 A1 | 12/2008 | Guracar et al. |
| 2008/0306386 A1 | 12/2008 | Baba et al. |
| 2008/0319317 A1 | 12/2008 | Kamiyama et al. |
| 2009/0010459 A1 | 1/2009 | Garbini et al. |
| 2009/0012393 A1 | 1/2009 | Choi |
| 2009/0016163 A1 | 1/2009 | Freeman et al. |
| 2009/0018445 A1 | 1/2009 | Schers et al. |
| 2009/0024039 A1 | 1/2009 | Wang et al. |
| 2009/0036780 A1 | 2/2009 | Abraham |
| 2009/0043206 A1 | 2/2009 | Towfiq et al. |
| 2009/0048519 A1 | 2/2009 | Hossack et al. |
| 2009/0069681 A1 | 3/2009 | Lundberg et al. |
| 2009/0069686 A1 | 3/2009 | Daft et al. |
| 2009/0069692 A1 | 3/2009 | Cooley et al. |
| 2009/0112095 A1 | 4/2009 | Daigle |
| 2009/0143680 A1 | 6/2009 | Yao et al. |
| 2009/0148012 A1 | 6/2009 | Altmann et al. |
| 2009/0150094 A1 | 6/2009 | Van Velsor et al. |
| 2009/0182237 A1 | 7/2009 | Angelsen et al. |
| 2009/0198134 A1 | 8/2009 | Hashimoto et al. |
| 2009/0203997 A1 | 8/2009 | Ustuner |
| 2009/0208080 A1 | 8/2009 | Grau et al. |
| 2009/0259128 A1 | 10/2009 | Stribling |
| 2009/0264760 A1 | 10/2009 | Lazebnik et al. |
| 2009/0306510 A1 | 12/2009 | Hashiba et al. |
| 2009/0326379 A1 | 12/2009 | Daigle et al. |
| 2010/0010354 A1 | 1/2010 | Skerl et al. |
| 2010/0016725 A1 | 1/2010 | Thiele |
| 2010/0063397 A1 | 3/2010 | Wagner |
| 2010/0063399 A1 | 3/2010 | Walker et al. |
| 2010/0069756 A1 | 3/2010 | Ogasawara et al. |
| 2010/0106431 A1 | 4/2010 | Baba et al. |
| 2010/0109481 A1 | 5/2010 | Buccafusca |
| 2010/0121193 A1 | 5/2010 | Fukukita et al. |
| 2010/0121196 A1 | 5/2010 | Hwang et al. |
| 2010/0130855 A1 | 5/2010 | Lundberg et al. |
| 2010/0168578 A1 | 7/2010 | Garson, Jr. et al. |
| 2010/0174194 A1 | 7/2010 | Chiang et al. |
| 2010/0217124 A1 | 8/2010 | Cooley |
| 2010/0240994 A1 | 9/2010 | Zheng |
| 2010/0249596 A1 | 9/2010 | Magee |
| 2010/0256488 A1 | 10/2010 | Kim et al. |
| 2010/0262013 A1 | 10/2010 | Smith et al. |
| 2010/0266176 A1 | 10/2010 | Masumoto et al. |
| 2010/0268503 A1 | 10/2010 | Specht et al. |
| 2010/0286525 A1 | 11/2010 | Osumi |
| 2010/0286527 A1 | 11/2010 | Cannon et al. |
| 2010/0310143 A1 | 12/2010 | Rao et al. |
| 2010/0324418 A1 | 12/2010 | El-Aklouk et al. |
| 2010/0324423 A1 | 12/2010 | El-Aklouk et al. |
| 2010/0329521 A1 | 12/2010 | Beymer et al. |
| 2011/0005322 A1 | 1/2011 | Ustuner |
| 2011/0016977 A1 | 1/2011 | Guracar |
| 2011/0021920 A1 | 1/2011 | Shafir et al. |
| 2011/0021923 A1 | 1/2011 | Daft et al. |
| 2011/0033098 A1 | 2/2011 | Richter et al. |
| 2011/0044133 A1 | 2/2011 | Tokita |
| 2011/0098565 A1 | 4/2011 | Masuzawa |
| 2011/0112404 A1 | 5/2011 | Gourevitch |
| 2011/0125017 A1 | 5/2011 | Ramamurthy et al. |
| 2011/0270088 A1 | 11/2011 | Shiina |
| 2012/0036934 A1 | 2/2012 | Kröning et al. |
| 2012/0057428 A1 | 3/2012 | Specht et al. |
| 2012/0095343 A1 | 4/2012 | Smith et al. |
| 2012/0095347 A1 | 4/2012 | Adam et al. |
| 2012/0116226 A1 | 5/2012 | Specht |
| 2012/0137778 A1 | 6/2012 | Kitazawa et al. |

FOREIGN PATENT DOCUMENTS

| | | |
|---|---|---|
| EP | 2182352 A2 | 5/2010 |
| EP | 2187813 A1 | 5/2010 |
| EP | 2198785 A1 | 6/2010 |
| EP | 1757955 B1 | 11/2010 |
| EP | 2356941 A1 | 8/2011 |
| EP | 1979739 | 10/2011 |
| EP | 2294400 | 2/2012 |
| EP | 1840594 B1 | 6/2012 |
| JP | 08-252253 | 10/1996 |
| JP | 2001-245884 A | 9/2001 |
| KR | 1020090103408 A | 10/2009 |
| WO | WO 92/18054 A1 | 10/1992 |
| WO | WO 98/00719 A2 | 1/1998 |
| WO | WO 2006/114735 A1 | 11/2006 |
| WO | WO 2007/127147 A2 | 11/2007 |
| WO | WO 2010/017445 A2 | 2/2010 |
| WO | WO 2010/095094 A1 | 8/2010 |

OTHER PUBLICATIONS

Cristianini et al.; An Introduction to Support Vector Machines; Cambridge University Press; pp. 93-111; 2000.
Du et al.; User parameter free approaches to multistatic adaptive ultrasound imaging; 5th IEEE International Symposium; pp. 1287-1290, May 2008.
Feigenbaum, Harvey, M.D.; Echocardiography; Lippincott Williams & Wilkins; Philadelphia; 5th Ed.; pp. 428, 484; 1993.
Haykin, Simon; Neural Networks: A Comprehensive Foundation (2nd Ed.); Prentice Hall; pp. 156-187; 1999.
Ledesma-Carbayo et al.; Spatio-temporal nonrigid registration for ultrasound cardiac motion estimation; IEEE Trans. on Medical Imaging; vol. 24; No. 9; Sep. 2005.
Leotta et al.; Quantitative three-dimensional echocardiography by rapid imaging . . . ; J American Society of Echocardiography; vol. 10; No. 8; ppl 830-839; Oct. 1997.
Morrison et al.; A probabilistic neural network based image segmentation network for magnetic resonance images; Proc. Conf. Neural Networks; Baltimore, MD; vol. 3; pp. 60-65; 1992.
Nadkarni et al.; Cardiac motion synchronization for 3D cardiac ultrasound imaging; Ph.D. Dissertation, University of Western Ontario; 2002.
Press et al.; Cubic spline interpolation; §3.3 in "Numerical Recipes in FORTRAN: The Art of Scientific Computing", 2nd Ed.; Cambridge, England; Cambridge University Press; pp. 107-110; 1992.

(56) References Cited

OTHER PUBLICATIONS

Sakas et al.; Preprocessing and volume rendering of 3D ultrasonic data; IEEE Computer Graphics and Applications; pp. 47-54, Jul. 1995.

Sapia et al.; Ultrasound image deconvolution using adaptive inverse filtering; 12 IEEE Symposium on Computer-Based Medical Systems, CBMS, pp. 248-253; 1999.

Sapia, Mark Angelo; Multi-dimensional deconvolution of optical microscope and ultrasound imaging using adaptive least-mean-square (LMS) inverse filtering; Ph.D. Dissertation; University of Connecticut; 2000.

Smith et al.; High-speed ultrasound volumetric imaging system. 1. Transducer design and beam steering; IEEE Trans. Ultrason., Ferroelect., Freq. Contr.; vol. 38; pp. 100-108; 1991.

Specht et al.; Deconvolution techniques for digital longitudinal tomography; SPIE; vol. 454; presented at Application of Optical Instrumentation in Medicine XII; pp. 319-325; 1984.

Specht et al.; Experience with adaptive PNN and adaptive GRNN; Proc. IEEE International Joint Conf. on Neural Networks; vol. 2; pp. 1203-1208; Orlando, FL; Jun. 1994.

Specht, D.F.; A general regression neural network; IEEE Trans. on Neural Networks; vol. 2.; No. 6; Nov. 1991.

Specht, D.F.; Blind deconvolution of motion blur using LMS inverse filtering; Lockheed Independent Research (unpublished); 1976.

Specht, D.F.; Enhancements to probabilistic neural networks; Proc. IEEE International Joint Conf. on Neural Networks; Baltimore, MD; Jun. 1992.

Specht, D.F.; GRNN with double clustering; Proc. IEEE International Joint Conf. Neural Networks; Vancouver, Canada; Jul. 16-21, 2006.

Specht, D.F.; Probabilistic neural networks; Pergamon Press; Neural Networks; vol. 3; pp. 109-118; 1990.

Von Ramm et al.; High-speed ultrasound volumetric imaging-System. 2. Parallel processing and image display; IEEE Trans. Ultrason., Ferroelect., Freq. Contr.; vol. 38; pp. 109-115; 1991.

Wells, P.N.T.; Biomedical ultrasonics; Academic Press; London, New York, San Francisco; pp. 124-125; 1977.

Widrow et al.; Adaptive signal processing; Prentice-Hall; Englewood Cliffs, NJ; pp. 99-116; 1985.

Specht et al.; U.S. Appl. No. 13/029,907 entitled "Point-Source Transmission and Speed-of-Sound Correction Using Multi-Aperture Ultrasound Imaging," filed Feb. 17, 2011.

Kramb et al,.; Considerations for using phased array ultrasonics in a fully automated inspection system. Review of Quantitative Nondestructive Evaluation, vol. 23, ed. D. O. Thompson and D. E. Chimenti, pp. 817-825, (month unavailable) 2004.

Sapia et al.; Deconvolution of ultrasonic waveforms using an adaptive wiener filter; Review of Progress in Quantitative Nondestructive Evaluation; vol. 13A; Plenum Press; pp. 855-862; (year of publication is sufficiently earlier than the effective U.S. filing date and any foreign priority date) 1994.

IMAGING WITH MULTIPLE APERTURE MEDICAL ULTRASOUND AND SYNCHRONIZATION OF ADD-ON SYSTEMS

CROSS REFERENCE TO RELATED APPLICATIONS

This application claims the benefit under 35 U.S.C. 119 of U.S. Provisional Patent Application No. 61/087,571, filed Aug. 8, 2008, titled "UNIVERSAL IMAGING AND SYNCHRONIZATION USING MULTIPLE APERTURE APPARATUS IN MEDICAL ULTRASOUND", and U.S. Provisional Patent Application Ser. No. 61/169,264, filed Apr. 14, 2009, titled "METHOD FOR AN ADD-ON MULTIPLE APERTURE PROCESSOR TO DETECT START AND DIRECTION OF PULSE FROM A HOST MACHINE", all which are herein incorporated by reference.

This application is related to U.S. patent application Ser. No. 11/532,013, filed Oct. 11, 2007, titled "METHOD AND APPARATUS TO VISUALIZE THE CORONARY ARTERIES USING ULTRASOUND" which claims priority to U.S. Provisional Patent Application No. 60/765,887, filed Feb. 6, 2006 titled "METHOD AND APPARATUS TO VISUALIZE THE CORONARY ARTERIES USING ULTRASOUND" and U.S. patent application Ser. No. 11/865,501, filed May 1, 2008, titled "METHOD AND APPARATUS TO PRODUCE ULTRASONIC IMAGES USING MULTIPLE APERTURES" which claims priority to U.S. Provisional Patent Application No. 60/862,951 filed Oct. 25, 2006, titled "METHOD AND APPARATUS TO PRODUCE ULTRASONIC IMAGES USING MULTIPLE APERTURES" and U.S. Provisional Patent Application No. 60/940,261, filed May 25, 2007, titled "METHOD AND APPARATUS TO PRODUCE ULTRASONIC IMAGES USING MULTIPLE APERTURES", all which are herein incorporated by reference.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates generally to imaging techniques used in medicine, and more particularly to medical ultrasound, and still more particularly to synchronizing an add-on apparatus to a host ultrasound machine for producing ultrasonic images using multiple apertures.

BACKGROUND OF THE INVENTION

In conventional ultrasonic imaging, a focused beam of ultrasound energy is transmitted into body tissues to be examined and the returned echoes are detected and plotted to form an image. In echocardiography the beam is usually stepped in increments of angle from a center probe position, and the echoes are plotted along lines representing the paths of the transmitted beams. In abdominal ultrasonography the beam is usually stepped laterally, generating parallel beam paths, and the returned echoes are plotted along parallel lines representing these paths. The following description will relate to the angular scanning technique for echocardiography (commonly referred to as a sector scan). However, the same concept with minor modifications can be implemented in abdominal scanners.

The basic principles of conventional ultrasonic imaging are well described in the first chapter of *Echocardiography*, by Harvey Feigenbaum (Lippincott Williams & Wilkins, 5$^{th}$ ed., Philadelphia, 1993). These will not be repeated here except as necessary to illustrate the differences between the conventional techniques and the present invention.

It is well known that the average velocity v of ultrasound in human tissue is about 1540 msec, the range in soft tissue being 1440 to 1670 m/sec (see for example P. N. T. Wells, *Biomedical Ultrasonics*, Academic Press, London, New York, San Francisco, 1977). Therefore, the depth of an impedance discontinuity generating an echo can be estimated as the round-trip time for the echo multiplied by v/2, and the amplitude is plotted at that depth along a line representing the path of the beam. After this has been done for all echoes along all beam paths, an image is formed. The gaps between the scan lines are typically filled in by interpolation.

In order to insonify the body tissues, a beam formed either by a phased array or a shaped transducer is scanned over the tissues to be examined. Traditionally, the same transducer or array is used to detect the returning echoes. This design configuration lies at the heart of one of the most significant limitations in the use of ultrasonic imaging for medical purposes; namely, poor lateral resolution. Theoretically the lateral resolution could be improved by increasing the aperture of the ultrasonic probe, but the practical problems involved with aperture size increase have kept apertures small and lateral resolution poor. Unquestionably, ultrasonic imaging has been very useful even with this limitation, but it could be more effective with better resolution.

In the practice of cardiology, for example, the limitation on single aperture size is dictated by the space between the ribs (the intercostal spaces). For scanners intended for abdominal and other use, the limitation on aperture size is not so obvious, but it is a serious limitation nevertheless. The problem is that it is difficult to keep the elements of a large aperture array in phase because the speed of ultrasound transmission varies with the type of tissue between the probe and the area of interest. According to the book by Wells (cited above), the speed varies up to plus or minus 10% within the soft tissues. When the aperture is kept small, the intervening tissue is, to a first order of approximation, all the same and any variation is ignored. When the size of the aperture is increased to improve the lateral resolution, the additional elements of a phased array may be out of phase and may actually degrade the image rather than improving it.

Instead of replacing the single transmit/receive ultrasound probes that are common in the medical industry, it would be advantageous and cost effective to increase the resolution of these devices with an add-on system. However, adding resolution to existing system would face additional challenges, such as synchronizing an add-on system to the existing host ultrasound machine.

SUMMARY OF THE INVENTION

The present invention relates generally to imaging techniques used in medicine, and more particularly to medical ultrasound, and still more particularly to synchronizing an add-on apparatus to a host ultrasound machine for producing ultrasonic images using multiple apertures.

One aspect of the invention provides an add-on ultrasound system, comprising an ultrasound receiver configured to receive ultrasound pulses transmitted from a host probe, a processor coupled to the ultrasound receiver, the processor comprising an algorithm configured to synchronize the add-on system to the host probe.

In some embodiments, the add-on ultrasound system can further include a display adapted to display ultrasound images from the processor. The display can be a GUI, for example.

In some embodiments, the add-on ultrasound system can include multiple ultrasound receivers, such as two, three, or even more ultrasound receiver.

One aspect of the invention provides an algorithm configured to process the received ultrasound pulses to synchronize the add-on system to the host ultrasound probe. In some embodiments, the algorithm can be adapted to calculate a start of frame of the transmitted ultrasound pulses. The start of frame can be calculated in a variety of ways. In some embodiments, the algorithm can calculate the start of frame by identifying an interval between amplitude peaks that is substantially larger than a pulse repetition interval. In other embodiments, the algorithm can calculate the start of frame by identifying a large change in peak amplitudes during successive scan lines. The large change in peak amplitudes can be from a low to a high or vice versa, for example.

In another aspect of the invention, the add-on ultrasound system can further comprise a tap that couples the host ultrasound probe to the add-on system. Since the tap has access to all the data from the host probe, the processor of the add-on ultrasound system can be adapted to process data from the tap to synchronize the add-on system to the host ultrasound probe.

Another aspect of the invention is a method of synchronizing an add-on ultrasound system to a host ultrasound probe, comprising, transmitting ultrasound pulses from the host ultrasound probe, receiving the ultrasound pulses with the add-on ultrasound system, and synchronizing the add-on ultrasound system to the host ultrasound probe with a processor.

In some embodiments, the receiving step further comprises receiving the ultrasound pulses with a receiving probe of the add-on ultrasound system. In other embodiments, the receiving step further comprises receiving the ultrasound pulses with a plurality of receiving probes of the add-on ultrasound system.

In some aspects of the invention, the synchronizing step further comprises synchronizing the add-on ultrasound system to the host ultrasound probe with the processor based on the transmitted ultrasound pulses. The add-on ultrasound system can be synchronized to the host ultrasound probe with an algorithm in the processor.

In some embodiments, the algorithm can calculate a start of frame of the transmitted pulses. The algorithm can calculate the start of frame by identifying an interval between amplitude peaks that is substantially larger than a pulse repetition interval. In another embodiment, the algorithm can calculate a start of frame by identifying a large change in peak amplitudes during successive scan lines. The peak amplitude changes can be from a low to a high or vice versa, for example.

In some embodiments, the synchronizing step can further comprise synchronizing the add-on ultrasound system to the host ultrasound probe with the processor adapted to process data from a tap that couples the host ultrasound probe to the add-on system.

Another aspect of the invention is providing ultrasound images to a display from the add-on ultrasound system. The ultrasound pulses can transmitted into tissue and the ultrasound images can be of the tissue.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

In the drawings.

DETAILED DESCRIPTION OF THE INVENTION

Various embodiments of an ultrasound imaging system are described.

Returned echoes in ultrasonography can be detected by a separate relatively non-directional receiving probe located away from the insonifying probe (e.g., the transmitting probe), and the non-directional receive transducer can be placed in a different acoustic window from the insonifying probe. This non-directional receiving probe can be called an omni-directional or receiving probe because it can be designed to be sensitive to a wide field of view.

If the echoes detected at the receiving probe are stored separately for every pulse from the insonifying transducer, the entire two-dimensional image can be formed from the information received by a single receiving probe. Additional copies of the image can be formed by additional omni-directional probes collecting data from the same set of insonifying pulses.

In one embodiment, an add-on device can be designed as a receive-only device while using an existing ultrasound machine from another manufacturer to act as the insonifying probe and transmit the ultrasound. A design of this type would allow the diagnostic laboratory or medical office to upgrade the B-mode, M-mode, or Doppler resolution of an existing machine without replacing it.

Figure 1A:
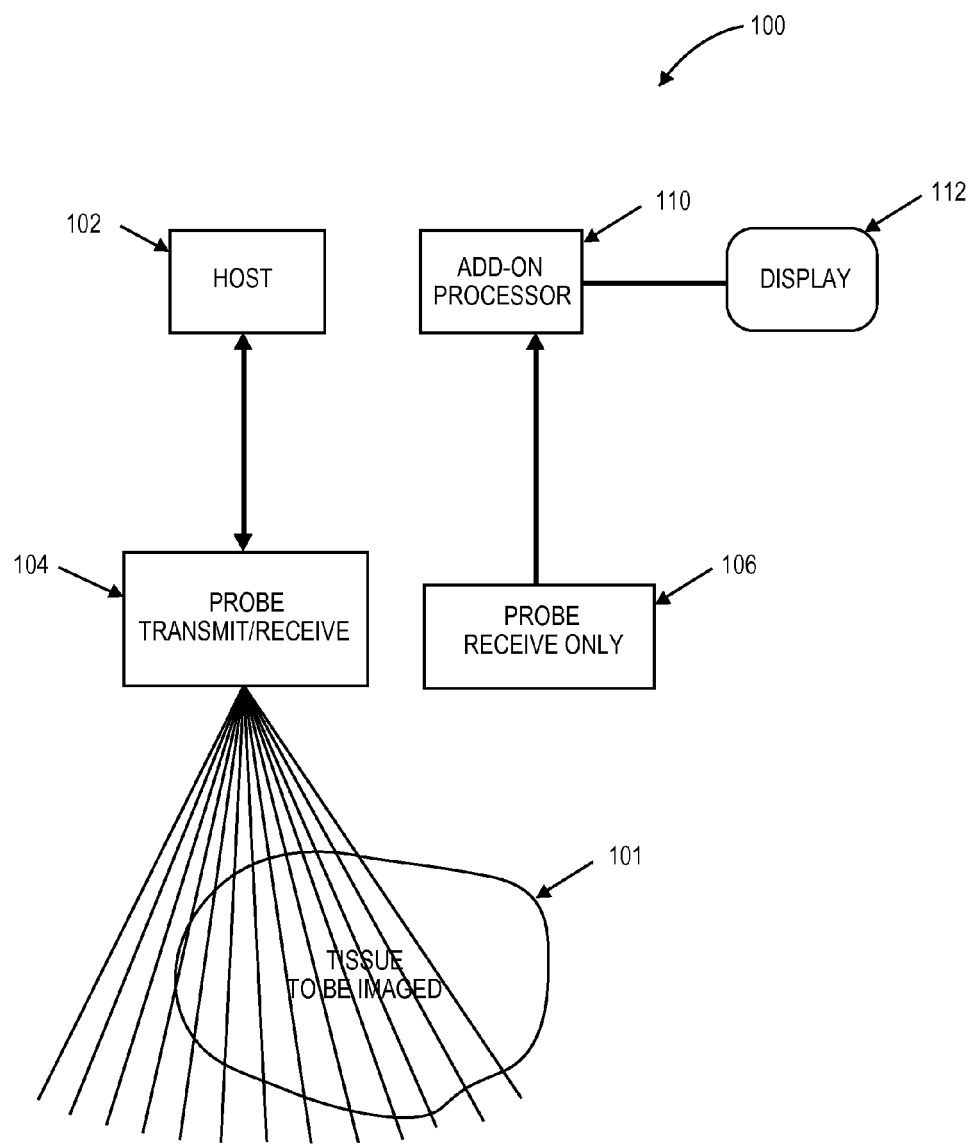
FIGS. 1A-1B illustrate add-on systems with single or multiple receive probes to be used with a host ultrasound machine for providing high-resolution ultrasound images.
Figure 1B:
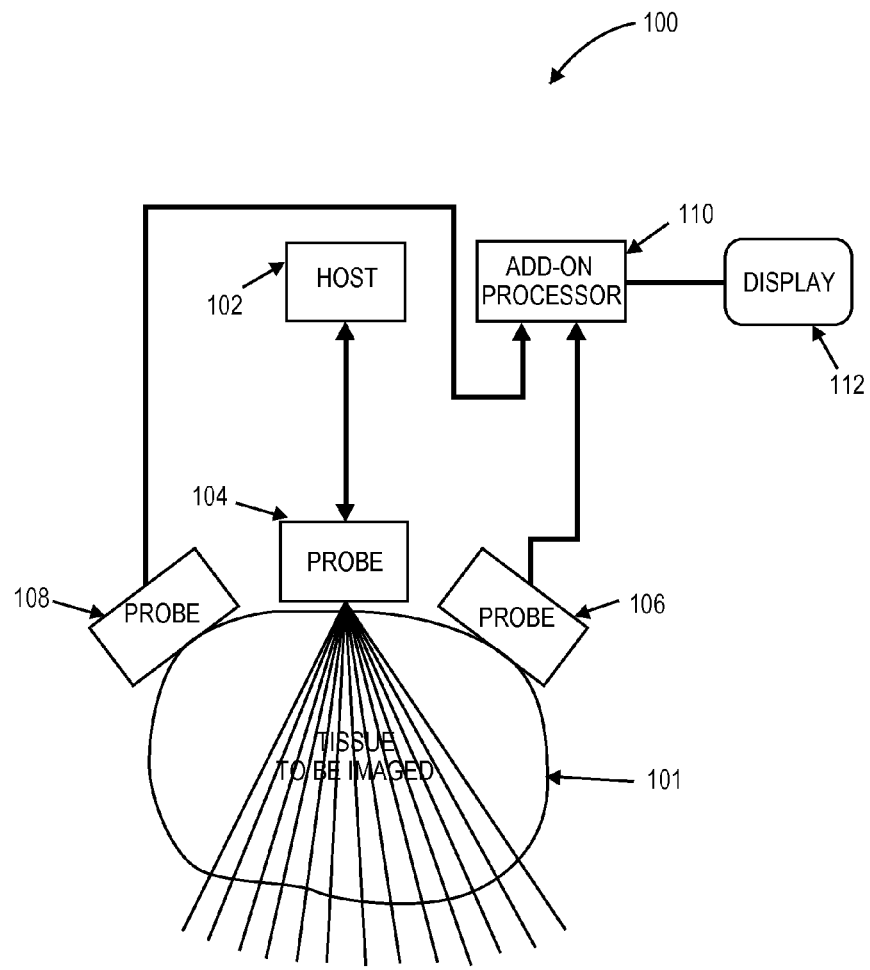

FIGS. 1A and 1B illustrate an external add-on system 100 for use with a host ultrasound system 102 and host transmit/receive probe 104 to image tissue 101. In FIG. 1A, the add-on system 100 includes a single receiving probe 106, and in FIG. 1B, the add-on system includes two receiving probes 106 and 108. The receiving probes 106 and 108 can have receive only capabilities, for example. In other embodiments, the receiving probes 106 and 108 can have transmit and receive capabilities. In other embodiments, the add-on system can include any number of receiving probes, such as three or more receiving probes. As shown in FIGS. 1A-1B, the add-on system 100 can further include add-on processor 110 and display 112. Display 112 can be a graphical user interface (GUI), or other appropriate display. Provision is made for time-gain-controls, overall gain, post-processing curves by means of soft buttons, compression levels, and depth of display. Other controls can conveniently be added to the display.

Synchronization of the receiving probes with the host probe is essential for the add-on system described herein. Without synchronizing the receiving probes to the host probe, the add-on system has no way of using the transmitted pulses from the host probe. Methods and algorithms for synchronizing the add-on system 100 to the host system 102 and host probe 104 can be implemented in add-on processor 110, which will be discussed below.

For the ultrasound systems described herein, the transmit functions can be handled by the host ultrasound system and host transmit/receive probe (e.g., a standard ultrasound machine), whereas the receive and display functions can be performed by the add-on system. In order for the add-on system to work with a majority of other manufacturer's current and future ultrasound devices (hereinafter to be referred to as the host system and host probe), it is necessary for the add-on system to deduce most of the properties of the host machine from the host machine or from the received ultrasound signals alone.

The first and most likely strongest pulses of ultrasound received will be directly from the transmit probe. These can easily be distinguished from echoes from deep tissues because they are first and strongest. From these received signals, the pulse repetition interval (PRI), the end of frame gap time, if any, the Total Frame Interval (TFI), and the maximum depth of penetration can be measured. The PRI, which corresponds to a time interval during which a scan line of echo data is collected, is defined as the elapsed time from the beginning of one pulse to the start of the next pulse. The maximum depth of penetration can be determined from the PRI and the known speed of sound in tissue. The actual depth of interest can be selected by a user of the system or can be a default percentage of the maximum depth of penetration.

An essential but more difficult parameter to estimate is the start time of the transmit pulse. Triggering on the first received pulse would be too noisy and would cause objectionable jitter from line to line resulting in degradation of the image. Assuming only that the PRI is a constant for a given set of settings on the host system, the estimated start time for the n'th line is simply the start time for the first line+(n−1)*(pulse repetition interval). It remains to estimate the start of the first line of a sector scan.

In FIGS. 1A-1B, the timing of the start of the transmit pulse from the host system and host probe can be deduced from the ultrasound pulses transmitted by the host probe and received by one of the receiving probes on either side of the host probe. The first detection of the transmit pulse will be delayed from the start of the transmit pulse because of the distance the transmit pulse has to travel to get to the receiving probe. However, that time delay can be calculated from the probe geometry and subtracted from the time that the pulse is first detected.

The main requirement for the measurement of the start of the transmit pulse is that the PRI be constant for a given set of settings and that a "flywheel" algorithm be used to estimate start of line in fixed repetition intervals. Because PRI is changed only infrequently, the estimation of PRI can be adapted over many scan cycles.

One embodiment of a method of synchronizing an add-on ultrasound system to a host ultrasound probe will now be described. Referring to add-on system 100 of FIGS. 1A-1B, host ultrasound probe 104 can transmit ultrasound pulses into tissue 101. The transmitted pulses can be received by the add-on system, such as by receiving probe 106. In some embodiments, such as in FIG. 1B, the add-on system can include a plurality of receiving probes for receiving the transmitted ultrasound signals (e.g., receiving probes 106 and 108). Add-on processor 110 can then synchronize the add-on system to the host ultrasound probe. The processor can use an algorithm or algorithms to synchronize the add-on system to the host probe. When the add-on system is synchronized to the host ultrasound probe, the add-on system can provide high-resolution images of the target tissue being imaged to a display, such as to a GUI.

Figure 2A:
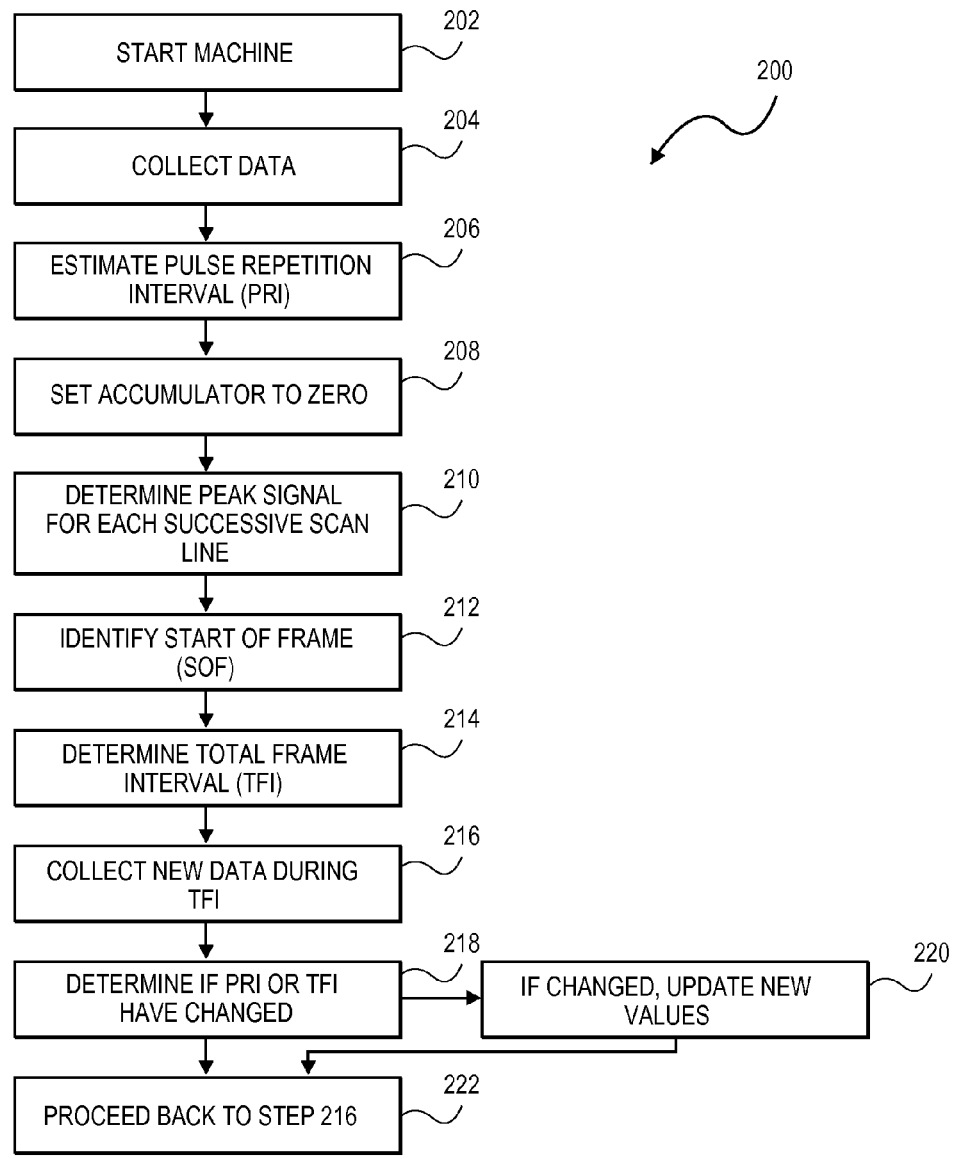
FIG. 2A is a flowchart showing one embodiment of a sequence of operations that an algorithm in an add-on system may use to synchronize the add-on system to a host ultrasound machine.
Figure 2B:
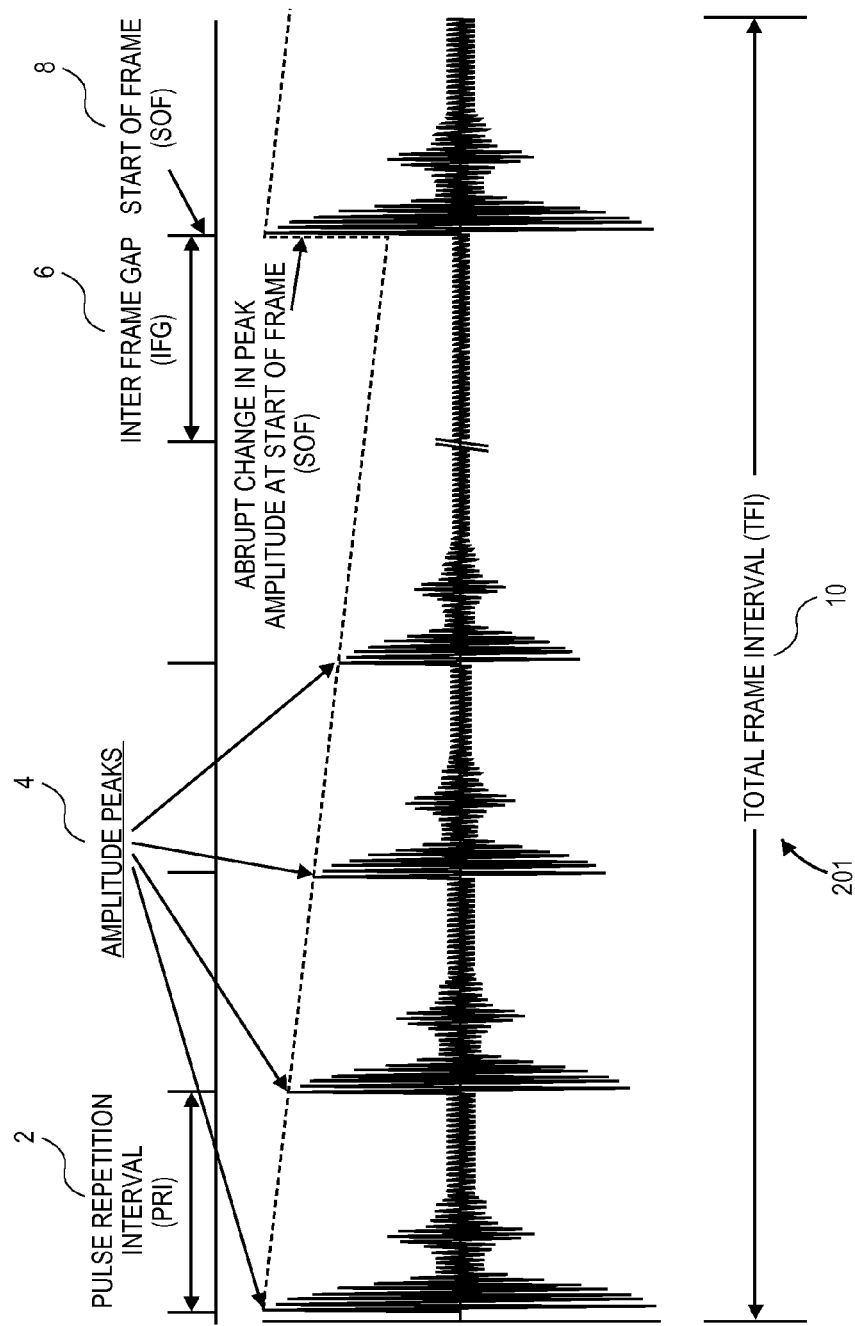
FIG. 2B is a plot illustrating the data collected by an add-on ultrasound system.

FIG. 2A shows a flowchart 200 illustrating one embodiment of a flywheel algorithm for determining the timing of the start of a transmit pulse from a host system. FIG. 2B shows a plot 201 illustrating a collection of data collected and used by the algorithm to synchronize an add-on system to a host machine. In FIG. 2B, the data collected can include PRI 2, Amplitude Peaks 4, IFG 6, SOF 8, and TFI 10. It should be understood that the algorithms described herein typically are executed by the add-on processor 110 described above. These algorithms can be programmed into the add-on processor as firmware, software, or hardware, or a combination of all three.

At step 202 of flowchart 200, the add-on system is started (i.e., powered or booted up).

At step 204, the add-on system begins to collect intervals of data. The data can be collected from the host probe, for example, or in some embodiments, from taps to the host probe. The data can be collected for several seconds, such as for approximately 1 to 2 seconds. The data collected will include intervals between peak amplitudes. The interval from one peak amplitude to the next peak amplitude occurrence corresponds to the PRI (see, for example, PRI 2 of FIG. 2B).

Next, at step 206 of flowchart 200, the PRI is estimated. As described above, the PRI is the elapsed time from the beginning of one pulse to the start of the next pulse. The PRI can be calculated by the add-on processor of the add-on system to be the median of the set of intervals collected during step 204.

Next, at step 208, the number of samples or pulses is counted by an accumulator function of the add-on processor. The accumulator function should be initialized to a value of zero before counting the number of sample times. The accumulator function is a counter of sample times which counts time for a total frame.

Next, at step 210, the algorithm in the add-on processor continues to collect intervals of data and determines a peak signal (see, for example, Amplitude Peaks 4 in FIG. 2B) for each successive set of scan line data.

At step 212, identify Start of Frame (SOF) by one of two methods. In the first embodiment, SOF occurs when the interval between amplitude peaks is substantially larger than the current PRI. This period is designated as the Inter Frame Gap (IFG). If the IFG cannot be distinguished from the PRI, then a second embodiment must be utilized to identify SOF. (see, for example, IFG 6 and PRI 2 in FIG. 2B).

In the second embodiment, the peak amplitude of successive lines are compared. As the host transmit angle sweeps across the frame, a small change in peak amplitude from line to line occurs. When the transmit angle shifts from the end-of-frame to the beginning-of-frame, there is a corresponding large change in peak amplitude. This change is used to identify SOF. See, for example, how the Amplitude Peaks 4 in FIG. 2B slowly change from line to line until a large change at SOF 8. The peak amplitudes can change from a low to a high, as shown in FIG. 2B, or vice versa.

At step 214, the add-on processor determines the total frame interval. The total frame interval is the interval between successive SOF times (in samples). See, for example, TOF 10 in FIG. 2B.

At step 216, the add-on system collects another set of data from.

At step 218, the algorithm in the add-on processor can determine if the PRI or TFI has changed. If changes are identified, the add-on system can update the new PRI and TFI values in 220.

At step 222, the add-on processor proceeds again to step 216 and continues to collect new data. The add-on processor continues to evaluate data at step 218 and updates the PRI and TFI if changes are identified.

Figure 3A:
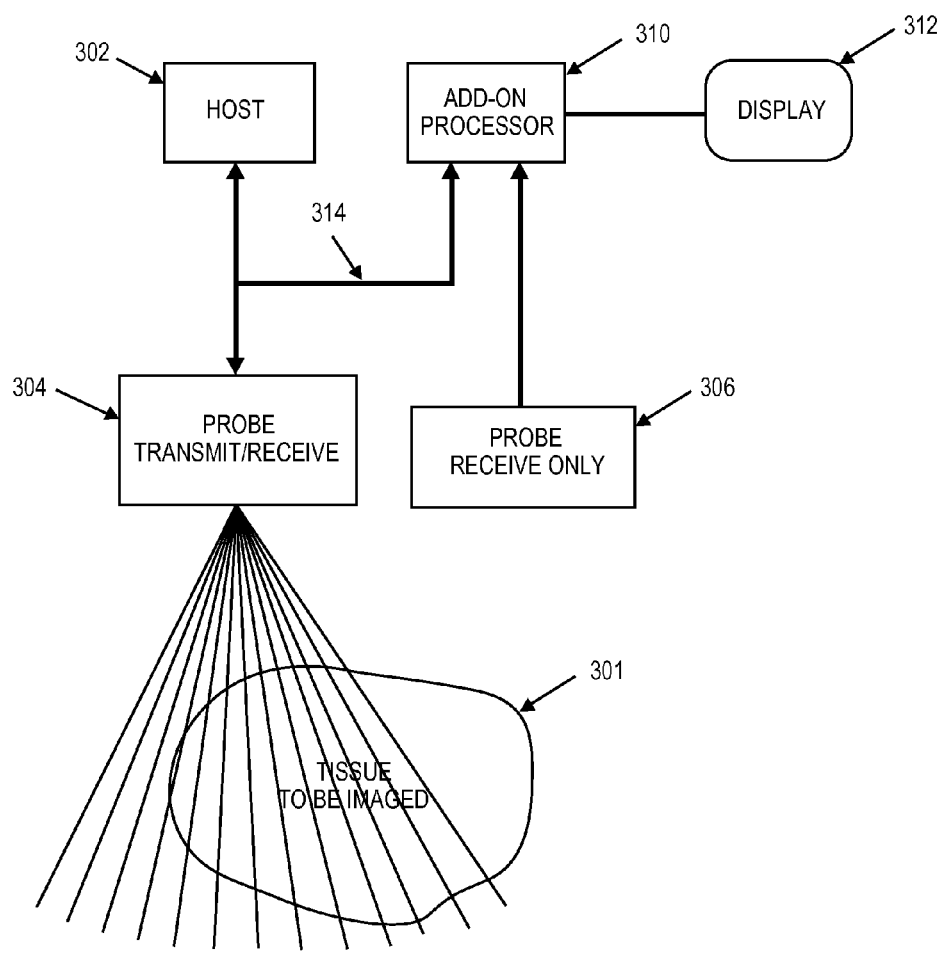
FIGS. 3A-3B illustrate add-on systems with single or multiple receive probes and high impedance taps to be used with a host ultrasound machine for providing high-resolution ultrasound images.
Figure 3B:
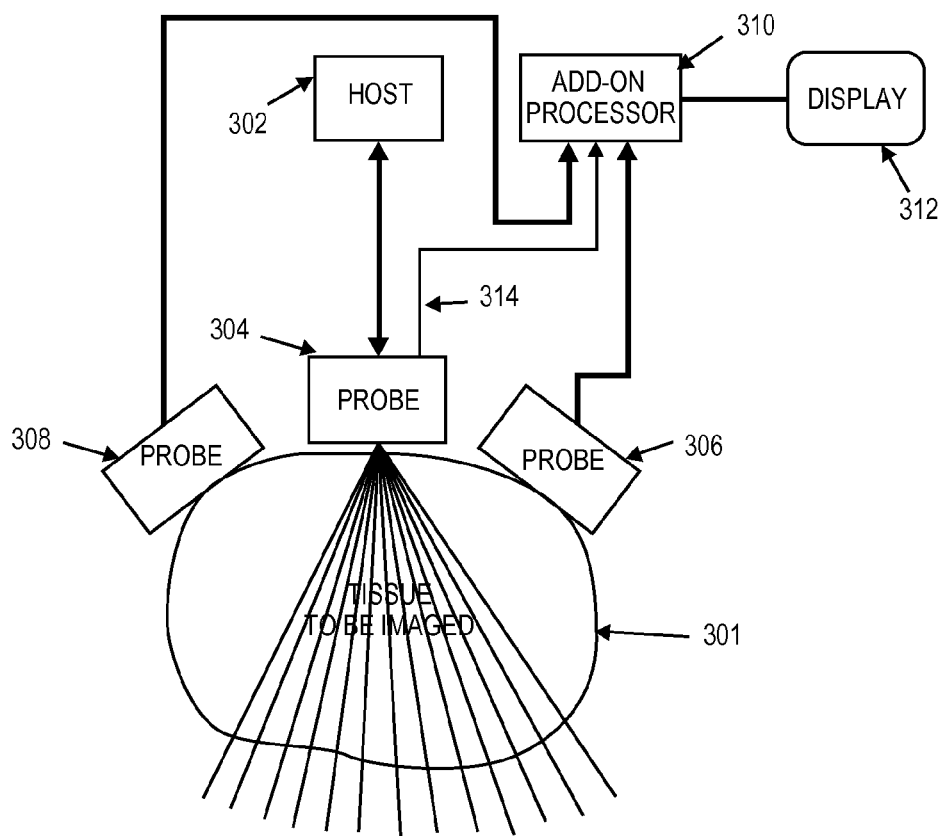

FIGS. 3A-3B illustrate another embodiment of an external add-on system 300 for use with a host ultrasound system 302 and host transmit/receive probe 304 to image tissue 301, the system further including high impedance taps 314 to connect the add-on system to the host system and probe. The taps 314 can be wires, for example. In FIGS. 3A-3B, host ultrasound system 302, host transmit/receive probe 304, receiving probes 306 and 308, add-on processor 310, and display 312 can correspond, respectively, to host ultrasound system 102, host transmit/receive probe 104, receiving probes 106 and 108, add-on processor 110, and display 112 of FIGS. 1A-1B. The taps 314 can connect from host probe 304 to add-on processor 310 to detect the start time and direction of the pulses transmitted from the host probe. In this configuration, all of the transmit pulses can be available to the add-on processor via the taps, instead of needing an algorithm to synchronize the add-on system to the host system as described above with reference to FIGS. 1A-1B and FIG. 2.

The taps 314 can wire into the transmit/receive probe of the host machine in order to detect directly the start of the transmit pulse. Also, by using this method, the direction of each transmitted pulse can be determined by monitoring the start pulse on a subset of two or more elements of the transmit array. In most current sector scan machines, the direction of the transmit beams progresses monotonically from one side of the sector to the other. In some advanced host machines, the beams may not be sent out in equal increments of angle from one pulse to the next, but instead may be transmitted in some interlaced order. When working with such a machine, it would be necessary to calculate the direction of each transmit pulse.

Another embodiment of a method of synchronizing an add-on ultrasound system to a host ultrasound probe will now be described. Referring to add-on system 300 of FIGS. 3A-3B, host ultrasound probe 304 can transmit ultrasound pulses into tissue 301. The transmitted pulses can be received by the add-on system, such as by receiving probe 306. In some embodiments, such as in FIG. 3B, the add-on system can include a plurality of receiving probes for receiving the transmitted ultrasound signals (e.g., receiving probes 306 and 308). Add-on processor 310 can then synchronize the add-on system to the host ultrasound probe using data from tap 314 that couples the host ultrasound probe to the add-on system. When the add-on system is synchronized to the host ultrasound probe, the add-on system can provide high-resolution images of the target tissue being imaged to a display, such as to a GUI.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A method of synchronizing an add-on ultrasound system to a host ultrasound probe, comprising:
   transmitting ultrasound pulses from the host ultrasound probe;
   receiving the ultrasound pulses with an add-on ultrasound receiver of the add-on ultrasound system, the add-on ultrasound system comprising an add-on ultrasound processor; and
   synchronizing the add-on ultrasound system to the host ultrasound probe with an algorithm in the add-on ultrasound processor, wherein the algorithm calculates a start of frame of the transmitted ultrasound pulses by identifying a large change in peak amplitudes during successive scan lines.

2. The method of claim 1 wherein the receiving step further comprises receiving the ultrasound pulses with a receiving probe of the add-on ultrasound system.

3. The method of claim 1 wherein the receiving step further comprises receiving the ultrasound pulses with a plurality of receiving probes of the add-on ultrasound system.

4. The method of claim 1 wherein the synchronizing step further comprises synchronizing the add-on ultrasound system to the host ultrasound probe with the add-on ultrasound processor based on the received ultrasound pulses alone.

5. The method of claim 1 wherein the synchronizing step further comprises synchronizing the add-on ultrasound system to the host ultrasound probe with the add-on ultrasound processor adapted to process data from a tap that couples the host ultrasound probe to the add-on system.

6. The method of claim 1 further comprising providing ultrasound images to a display from the add-on ultrasound system.

7. The method of claim 1 wherein the transmitting step further comprises transmitting the ultrasound pulses into tissue.

8. A method of synchronizing an add-on ultrasound system to a host ultrasound probe, comprising:
   transmitting ultrasound pulses from the host ultrasound probe;
   receiving the ultrasound pulses with an add-on ultrasound receiver of the add-on ultrasound system, the add-on ultrasound system comprising an add-on ultrasound processor; and
   synchronizing the add-on ultrasound system to the host ultrasound probe with an algorithm in the add-on ultrasound processor, wherein the algorithm calculates a start of frame of the transmitted ultrasound pulses by identifying when a peak amplitude changes from a low to a high or vice versa.

9. The method of claim 8 wherein the receiving step further comprises receiving the ultrasound pulses with a receiving probe of the add-on ultrasound system.

10. The method of claim 8 wherein the receiving step further comprises receiving the ultrasound pulses with a plurality of receiving probes of the add-on ultrasound system.

11. The method of claim 8 wherein the synchronizing step further comprises synchronizing the add-on ultrasound system to the host ultrasound probe with the add-on ultrasound processor based on the received ultrasound pulses alone.

12. The method of claim 8 wherein the synchronizing step further comprises synchronizing the add-on ultrasound system to the host ultrasound probe with the add-on ultrasound processor adapted to process data from a tap that couples the host ultrasound probe to the add-on system.

13. The method of claim 8 further comprising providing ultrasound images to a display from the add-on ultrasound system.

14. The method of claim 8 wherein the transmitting step further comprises transmitting the ultrasound pulses into tissue.

15. An add-on ultrasound system, comprising:
an add-on ultrasound receiver configured to receive ultrasound pulses transmitted from a host probe;
an add-on processor coupled to the add-on ultrasound receiver, the add-on processor comprising an algorithm configured to synchronize the add-on system to the host probe, wherein the algorithm is adapted to calculate a start of frame of the transmitted ultrasound pulses by identifying a large change in peak amplitudes during successive scan lines.

16. The add-on ultrasound system of claim 15 further comprising a display adapted to display ultrasound images from the add-on processor.

17. The add-on ultrasound system of claim 15 further comprising a second add-on ultrasound receiver.

18. The add-on ultrasound system of claim 15 wherein the algorithm is configured to synchronize the add-on system to the host ultrasound probe based on the received ultrasound pulses alone.

19. The add-on ultrasound system of claim 15 further comprising a tap coupling the host ultrasound probe to the add-on system.

20. The add-on ultrasound system of claim 19 wherein the add-on processor is adapted to process data from the tap to synchronize the add-on system to the host ultrasound probe.

21. An add-on ultrasound system, comprising:
an add-on ultrasound receiver configured to receive ultrasound pulses transmitted from a host probe;
an add-on processor coupled to the add-on ultrasound receiver, the add-on processor comprising an algorithm configured to synchronize the add-on system to the host probe, wherein the algorithm is adapted to calculate a start of frame of the transmitted ultrasound pulses by identifying when a peak amplitude changes from a low to a high or vice versa.

22. The add-on ultrasound system of claim 21 further comprising a display adapted to display ultrasound images from the add-on processor.

23. The add-on ultrasound system of claim 21 further comprising a second add-on ultrasound receiver.

24. The add-on ultrasound system of claim 21 wherein the algorithm is configured to synchronize the add-on system to the host ultrasound probe based on the received ultrasound pulses alone.

25. The add-on ultrasound system of claim 21 further comprising a tap coupling the host ultrasound probe to the add-on system.

26. The add-on ultrasound system of claim 25 wherein the add-on processor is adapted to process data from the tap to synchronize the add-on system to the host ultrasound probe.

* * * * *